United States Patent
Coninx

(10) Patent No.: US 10,292,626 B2
(45) Date of Patent: May 21, 2019

(54) METHOD AND DEVICE FOR CONDUCTING A PURE TONE AUDIOMETRY SCEENING

(71) Applicant: Karin Coninx-Wittgens, Solingen (DE)

(72) Inventor: Frans Coninx, Solingen (DE)

(73) Assignee: JACOTI BVBA, Wevelgem (BE)

( * ) Notice: Subject to any disclaimer, the term of this patent is extended or adjusted under 35 U.S.C. 154(b) by 125 days.

(21) Appl. No.: 14/346,501

(22) PCT Filed: Sep. 18, 2012

(86) PCT No.: PCT/EP2012/068377
§ 371 (c)(1),
(2) Date: Mar. 21, 2014

(87) PCT Pub. No.: WO2013/041538
PCT Pub. Date: Mar. 28, 2013

(65) Prior Publication Data
US 2014/0236043 A1    Aug. 21, 2014

(30) Foreign Application Priority Data

Sep. 21, 2011  (EP) ..................................... 11182209

(51) Int. Cl.
*A61B 5/12*      (2006.01)
*A61B 5/0484*    (2006.01)

(52) U.S. Cl.
CPC .......... *A61B 5/123* (2013.01); *A61B 5/04845* (2013.01); *A61B 5/121* (2013.01)

(58) Field of Classification Search
CPC ........ A61B 5/12; A61B 5/123; A61B 5/04845
See application file for complete search history.

(56) References Cited

U.S. PATENT DOCUMENTS

| 3,221,100 A | | 11/1965 | Towne | |
|---|---|---|---|---|
| 3,781,491 A | * | 12/1973 | Biondi | ................. H04R 25/353 381/150 |
| 4,615,007 A | * | 9/1986 | King | ........................ A61B 5/12 600/559 |
| 5,105,822 A | * | 4/1992 | Stevens | .................... A61B 5/12 600/559 |

(Continued)

OTHER PUBLICATIONS

International Search Report for corresponding International PCT Application No. PCT/EP2012/068377, dated Nov. 6, 2012.

*Primary Examiner* — Sean O Dougherty
(74) *Attorney, Agent, or Firm* — Workman Nydegger

(57) ABSTRACT

A screening device for conducting a tone audiometry includes a tone generator, an input device, and a controller device. The controller device is arranged to repeatedly perform: selecting a test stimulus from a group of test stimuli; applying the selected test stimulus to a test person; receiving via the input device from the test person a response indicating which test stimulus was heard by the test person; and adjusting an intensity according to the received response for selecting a next test stimulus. The group of test stimuli includes (i) no tone at all, (ii) a single tone with a first frequency and a first given intensity, and (iii) a multitude of tones of a second frequency and a second given intensity. The second frequency is higher than the first frequency and the multitude of tones have a duration shorter than the duration of the single tone.

17 Claims, 2 Drawing Sheets

(56) References Cited

U.S. PATENT DOCUMENTS

| Patent/Pub. No. | | Date | Inventor | Classification |
|---|---|---|---|---|
| 5,746,205 | A * | 5/1998 | Virsu | A61B 5/12 600/544 |
| 5,792,073 | A * | 8/1998 | Keefe | A61B 5/121 600/559 |
| 6,048,320 | A * | 4/2000 | Brainard, II | A61B 1/227 600/559 |
| 6,379,314 | B1 * | 4/2002 | Horn | A61B 5/121 600/559 |
| 6,876,750 | B2 * | 4/2005 | Allred | H04R 25/70 381/314 |
| 7,016,504 | B1 * | 3/2006 | Shennib | A61B 5/121 381/60 |
| 8,014,870 | B2 * | 9/2011 | Seidman | A61N 1/361 600/411 |
| 2002/0165466 | A1 * | 11/2002 | Givens | A61B 5/121 600/559 |
| 2002/0183648 | A1 * | 12/2002 | Hou | H04M 1/2475 600/559 |
| 2003/0165247 | A1 * | 9/2003 | Bantz | H04R 25/70 381/312 |
| 2003/0215105 | A1 * | 11/2003 | Sacha | H04R 25/505 381/312 |
| 2004/0006283 | A1 * | 1/2004 | Harrison | A61B 5/12 600/559 |
| 2004/0049125 | A1 * | 3/2004 | Nakamura | A61B 5/0002 600/559 |
| 2004/0071304 | A1 * | 4/2004 | Yanz | H04R 25/70 381/312 |
| 2004/0152998 | A1 * | 8/2004 | Stott | A61B 5/742 600/559 |
| 2005/0018858 | A1 * | 1/2005 | John | A61B 5/121 381/60 |
| 2005/0033193 | A1 * | 2/2005 | Wasden | A61B 5/121 600/559 |
| 2005/0070815 | A1 * | 3/2005 | Shahrestani | A61B 5/1104 600/559 |
| 2006/0215845 | A1 * | 9/2006 | Burleigh | A61B 5/00 381/60 |
| 2007/0129649 | A1 * | 6/2007 | Thornton | A61B 5/121 600/559 |
| 2007/0135730 | A1 * | 6/2007 | Cromwell | A61B 5/121 600/559 |
| 2007/0179398 | A1 | 8/2007 | Margolis | |
| 2009/0163828 | A1 * | 6/2009 | Turner | A61B 5/04845 600/559 |
| 2009/0259140 | A1 * | 10/2009 | Buchman | A61B 5/121 600/559 |
| 2009/0262969 | A1 * | 10/2009 | Short | H04R 3/005 381/370 |
| 2009/0326405 | A1 * | 12/2009 | Makinen | A61B 5/04845 600/544 |
| 2010/0016755 | A1 * | 1/2010 | Henry | A61B 5/121 600/559 |
| 2010/0020988 | A1 * | 1/2010 | McLeod | H03G 5/025 381/107 |
| 2010/0217149 | A1 | 8/2010 | Harrison et al. | |
| 2010/0254551 | A1 * | 10/2010 | Aoki | H04R 25/505 381/312 |
| 2011/0046511 | A1 * | 2/2011 | Koo | A61B 5/121 600/559 |
| 2011/0190658 | A1 * | 8/2011 | Sohn | A61B 5/00 600/559 |
| 2012/0029383 | A1 * | 2/2012 | Henriksen | A61B 5/12 600/559 |
| 2012/0130271 | A1 * | 5/2012 | Margolis | A61B 5/123 600/559 |
| 2012/0157876 | A1 * | 6/2012 | Bang | A61B 5/123 600/559 |
| 2012/0232422 | A1 * | 9/2012 | Donofrio | A61B 5/4821 600/559 |
| 2012/0283594 | A1 * | 11/2012 | Uhlen | A61B 3/113 600/559 |
| 2013/0231581 | A1 * | 9/2013 | Kallstrand | A61B 5/04845 600/544 |
| 2014/0194775 | A1 * | 7/2014 | Van Hasselt | A61B 5/123 600/559 |
| 2014/0236043 | A1 * | 8/2014 | Coninx | A61B 5/123 600/559 |
| 2014/0243913 | A1 * | 8/2014 | Lineaweaver | A61N 1/36032 607/3 |
| 2014/0309549 | A1 * | 10/2014 | Selig | H04R 1/1041 600/559 |

* cited by examiner

METHOD AND DEVICE FOR CONDUCTING A PURE TONE AUDIOMETRY SCEENING

BACKGROUND

The invention refers to a method for conducting a pure tone audiometry, using tones of different frequency and intensity, utilizing an adaptive procedure.

SUMMARY

A tone audiometry method is used to measure the capability of a test person to identify tones of a different frequency. This is especially important in the frequency range between 500 and 4.000 Hz as this is the frequency range of normal conversation. Pure tone audiometry therefore is the key hearing test used to identify hearing threshold levels of an individual person, enabling determination of the degree of a hearing loss of different frequencies. As an example, the hearing threshold level might be 0 dB at 500 Hz, corresponding to normal hearing sensitivity, but 60 dB at 4.000 Hz, corresponding to a hearing loss of 60 dB. Pure tone audiometry as it is used until now is a subjective, behavioural measurement of the hearing threshold as it relies on patient response to the pure tone stimuli. Therefore, pure tone audiometry is used on adults and children old enough to cooperate with the test procedure. In pure tone audiometry, calibrated audiometry headphones are being used, sounds are presented by using a pure tone audiometer whereas a tone is presented by the test leader and the test person is expected to respond to this by pushing a button, raising the hand, giving a voice signal or, for children, by performing an action in a play situation (play audiometry in children).

A quality of the assessed pure tone thresholds, that is the lowest level that was heard by the patient, not only depends on the reliability of the test persons responses, but also very strongly on the competencies and experience of test leader.

This form of audiometry is the gold standard for diagnostic procedures in clinics, but it does not fulfill the basic requirements for screening, that is a fast, reliable, easy and cheap procedure, not depending on competencies and experience of the test leader. As the number of people with a hearing disorder is still improving, there is a need for such a fast, easy and cheap screening procedure, not being dependent from the competencies and experience of a test leader.

This need is met by the invention, providing a method and a device for conducting a pure tone audiometry, using tones of different frequency and intensity utilizing an adaptive procedure without being dependent on a test leader. The invention is characterized in claim 1 and the subsequent claims.

More specifically, a method for conducting a pure tone audiometry, using tones of different frequency and intensity utilizing an adaptive procedure is provided, where tone signals with at least two different frequencies are being independently changed by delivering to test person a set of at least three different test stimuli, those test stimuli being selected from a group of no tone at all, one long tone with a first frequency and a multitude, preferably three, short tones of a second frequency. This second frequency is higher than the first frequency. According to the method, a response from the test person is received, said response corresponding to one of the different test stimuli. After receipt of that response, a next test stimulus is presented to the test person after a short delay, preferably half a second to a second after the test persons response. In case the answer of the test person was correct and if the test stimulus did include a tone at all, the next test stimulus of that frequency will have a lower intensity. On the other hand, the next test stimulus of that frequency will have a higher intensity in case the answer was not correct. In any case, the next test stimulus being delivered to the test person, following an answer, may utilize a different frequency, such further improving the accuracy of the test result.

It has proven advantageous to interpret a wrong response of the test person and to deliver the next test stimulus in case the test person did not respond after being informed that a response is expected within a predefined period of time, preferably within four to five seconds.

Preferably, the test stimulus, following an answer, is randomly selected from the group of available test stimuli. The possible answers may be visualized to the test person, i.e. by pictograms.

It is a specific advantage when outlier values that may occur after a phase of disturbing ambient noise or a short loss of concentration of the test person are removed from the threshold calculation, following the test routine. In that respect, it is an additional advantage when the ambient noise is measured during the delivery of the test stimulus and the method is rejecting the response of the test person in case the ambient noise and the test stimulus are of sufficiently similar frequency and the intensity of the ambient noise is of a similar or higher intensity than the test stimulus. A value may be characterized as an outlier value if it is more than the step size in the procedure away from the previous calculated threshold value (following the test routine), said step size being preferably in the range between 5 and 10 dB.

It is most efficient to utilize no more than three different frequencies in one test run.

What is also provided is a device for conducting an automated pure tone audiometry screening, comprising a tone generator, being capable of delivering pure tones of different frequencies and intensities as well as being able to deliver tones either as a long tone or a set of shorter tones, also comprising a set of at least three response buttons and an electronic device, being able to conduct a method as described above. That device according may either comprise an air-conduction transducer or a bone-conduction transducer.

Usability is improved when the response buttons of the device are software implemented buttons on a touch screen, such being adaptable to the test person, i.e. the age of the test person.

An additional advantage can be achieved when the device comprises a microphone for measuring the ambient noise and an electronic device, being capable of conducting the ambient noise based trial rejection method as described above.

BRIEF DESCRIPTION OF THE DRAWINGS

A typical example of the invention is explained, utilizing the following figures.

DETAILED DESCRIPTION OF VARIOUS EMBODIMENTS

Figure 1:
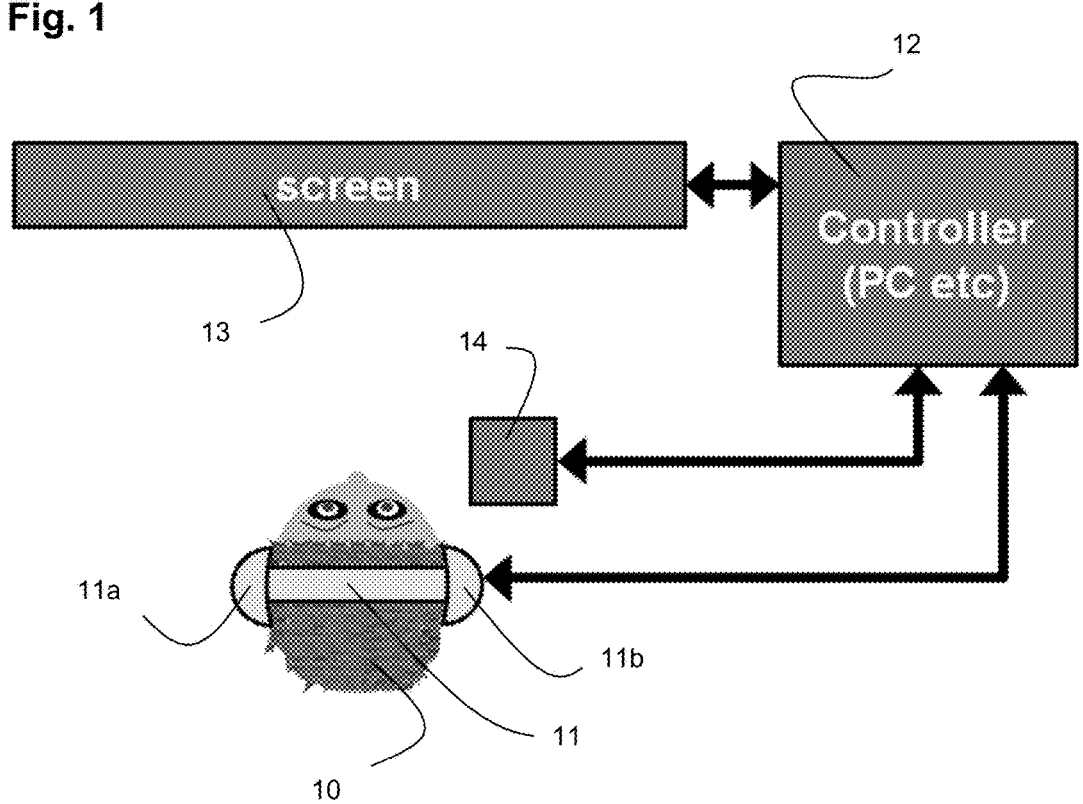
FIG. 1 shows a principle test setup.

FIG. 1 shows the principle test setup, in which the invention is used. A test person 10 is wearing headset 11 with a left 11a and a right 11b speaker. The speakers 11a, 11b can be utilized together or one by one in order to test the hearing ability of the two ears separately.

An electronic device 12 is providing the necessary hard- and software in order to conduct the inventive method whereas a screen 13 is used to visualize commands and expected answers to the test person. Finally, an input device 14, typically a mouse or a button array, is shown, to be used by the test person to provide its input to the system.

The headset, the screen and the input device are connected to the electronic device, whereas this connection may be a wired or a wireless connection.

The human interface devices used, that is the screen, the input device and the headset, need not to be separate devices. For example, the screen and the input device can be combined by using a touchpad computer or even a mobile device with a touch screen. In case the acoustic conditions in the surrounding as well as the speakers in the device are sufficiently good, such speakers could be used in combination with one of the two other human interface devices. It will also be possible to use a touchpad device with integrated speakers as an all-in-one human interface device for conducting the inventive method, also including the electronic device running the respective software.

Figure 2:
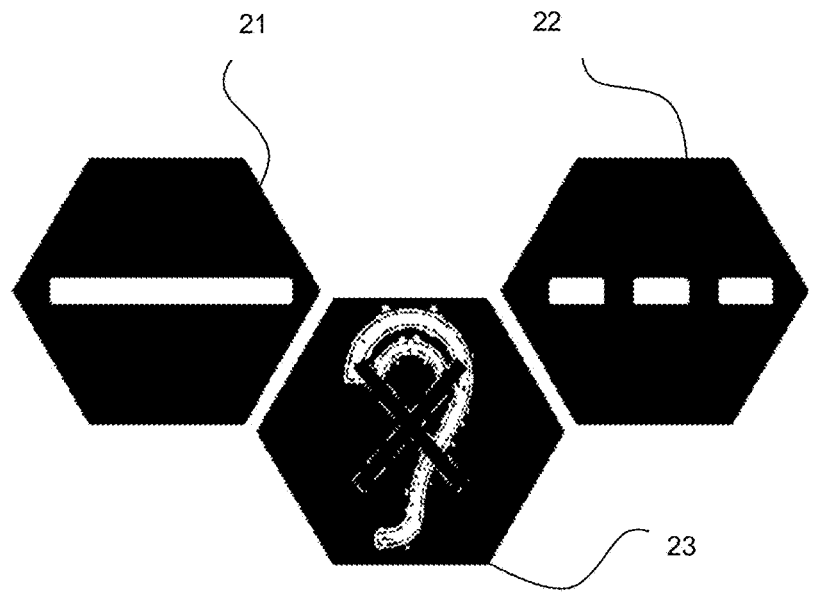
FIG. 2 shows a typical screen layout presented to a test person.

Other than methods used in the prior art, the invention utilizes tones of at least two different frequencies in the same test run, integrated in different test stimuli, in addition to a test stimulus with "no tone at all". A tone in the framework of this invention is not only a pure tone with a specific intensity of one specific frequency, but may also be a narrow band of noise with a specific intensity, centered at such a frequency. For example and as shown in FIG. 2, three different test stimuli may be used: first, a test stimulus 21 comprising a single long tone of a first frequency, second, a set of three short tones 22 with a second frequency and third, nothing at all 23. The second frequency is always higher than the first frequency. The third option, nothing heard, is important when it comes to the reduction of guesses by the test person.

The picture shown in FIG. 2 may be visualized on a touch screen. According to the inventive method, a first test stimulus, for example a long tone with a frequency of 500 Hz, is presented to the test person. This tone may have an intensity of 60 dB.

Once the test stimulus has been presented to the test person, the system automatically informs the test person that an answer is expected. This may be done for example by changing the color of the buttons 21, 22 and 23 or by displaying a message on the screen, by another optical or tactile signal or in any other way feasible.

The test person than has to present his answer by pressing one of the buttons 21, 22 or 23, whereas the correct choice in the present example would be to press button 21.

Once the test person has presented his answer to the system, the next stimulus is presented to the test person automatically after a short delay, that delay typically being in the order between half a second and a second.

Should there be no answer of the test person within a predetermined period of time, typically four to five seconds, the answer is rated wrong. The same it true, if the pressed button does not correspond to the tone stimulus presented to the test person.

The next tone stimulus presented to the test person is selected randomly from the set of available test stimuli. In the present example, it may be again one single longer tone with the first frequency, a set of three shorter tones with the second frequency, or nothing. Choosing the next text stimulus randomly provides the advantage that there is no order of the test stimuli which could be recognized by the test person. Such a recognition could lead to wrong and unrealistic test results.

In case the answer as a response to test stimulus 1 was correct, the next presentation of a test stimulus with that same frequency will utilize a lower intensity. In screening devices, the step width would usually be 10 dB, so that the next test stimulus utilizing the first frequency, presented to the test person would have an intensity of 50 dB in the present example. This new intensity is used for the next test stimulus of exactly that first frequency and is independent from intensities used in test stimuli for other frequencies, here for the second frequency. Therefore, it is possible that two consecutive test stimuli utilize completely different intensities. A first test stimulus with a first frequency may for example utilize an intensity of 10 dB whereas the next consecutive test stimulus with a set of three tones with a second frequency may utilize an intensity of 60 dB.

Usually, two frequencies are used in one screening round, but it is also possible to use more than two frequencies in parallel. Thus additional tones could be integrated either in the setup shown in FIG. 2, that is one long tone with a lower frequency and three short tones with a higher frequency, or by utilizing different stimuli, for example one long tone, two, four and six short tones when utilizing four different frequencies.

The test procedure for each separate frequency works as follows: once the test person has prompted a correct answer to a test stimulus with a set frequency, the next test stimulus of that frequency is presented with a lower intensity, usually with a step size of 10 dB. Once the test person has presented a wrong answer, the next stimulus presented to the test person with that frequency is higher again, usually twice the normal step size. In that example, the next test stimulus would have an intensity of 30 dB, assuming that the lowest intensity heard was at 20 dB. This procedure is usually repeated three times so that three lower hearing thresholds are determined for each frequency utilized.

In that way, the lowest intensity, just to be heard by the test person, can be reliably determined. Once, the system has found the lowest intensity for the same frequency for the third time the method is ended and the result, the threshold, is calculated from those three measured intensity levels, usually calculating the arithmetic median plus half step size.

The method can be further improved by excluding outlier values. Those outlier values can be produced by the test person, as a test person might loose concentrating during the test, therefore responding unintentionally wrong, thus producing incorrect test results.

In addition, the specific measurement may be disturbed by other noises from outside. Therefore, the method may utilize the input of an additional microphone (not shown), measuring the surrounding noise. Should the surrounding noise be in the order or higher than the intensity of the test stimulus, and in addition cover the same frequency range as the coincident tone stimulus, the respective test result may be discarded. The same is true for outlier values that are more than two steps away from the average of the other measured thresholds.

In typical screening system, those outlier values may be discarded once the measurement has been completed so that the measured result depends on two measured thresholds only instead of three, as the third one has been discarded.

A further improvement of the invention is to discard those outlier values during the running measurement already so that the screening run is continued until three valid thresholds have been measured for each frequency/tone stimulus.

A usual measurement with two test frequencies does converge quickly and is finished in a time between 50 and 80 seconds.

Figure 3:
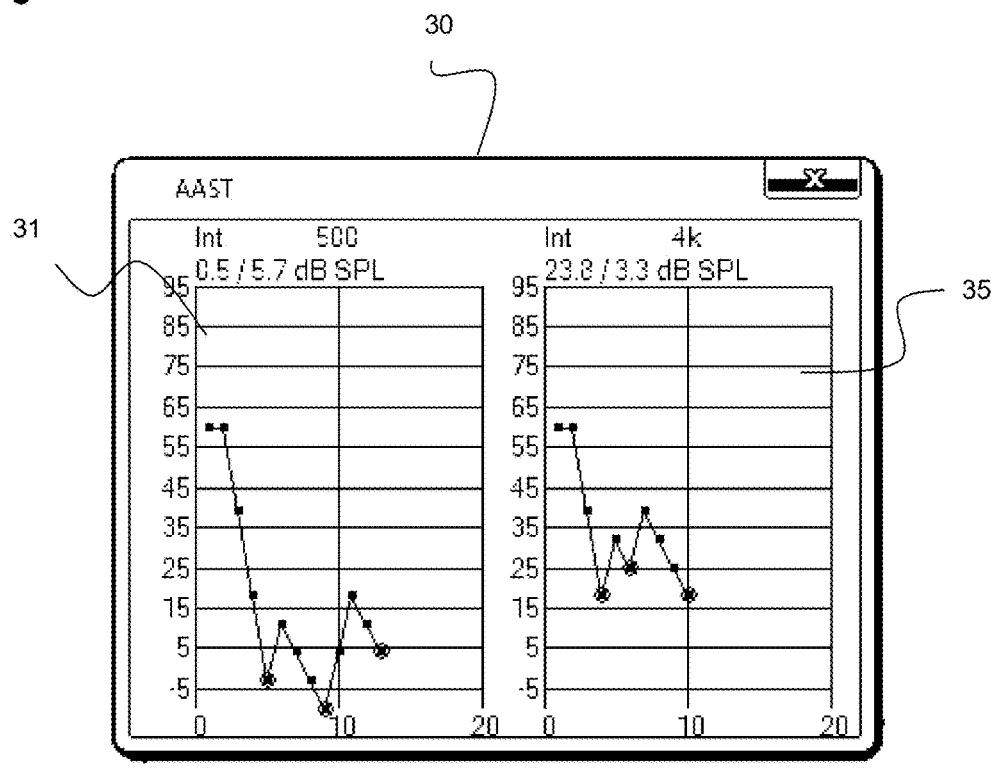
FIG. 3 shows a typical result for the two tone version of the invention.

Usually, one test run, utilizing two tones, for example 500 Hz and 4 kHz, is sufficient. An example of such a test result is shown in FIG. 3, showing a complete audiogram 30 with a first result 31 for the first frequency (500 Hz) and 35 for a second frequency (4 kHz). The three threshold values for the first frequency lie around zero, whereas the three threshold values for the second frequency a grouped around 22 dB, leading to the result that the test person has a normal hearing ability for frequency around 500 Hz and a hearing disorder of about 22 dB at 4 kHz. If more accurate results are necessary, the test run may be repeated, utilizing two different frequencies, typically 1 and 2 kHz.

A meta-level procedure may also be implemented and can be used on demand also: a first test is started using 500 Hz and 4 kHz. In case thresholds at both frequencies are ok, the procedure stops. In case thresholds at one or both frequencies are not ok, a subsequent test procedure using frequencies of 1 kHz and 2 kHz is started.

Those pure tone audiometric methods like the inventive method usually do not test frequencies above 8 kHz as those frequencies are not necessary in order to understand spoken words. Nevertheless, such high resolution tests can be utilized with the inventive method also, provided that the test setup is sufficiently precise.

The invention claimed is:

1. A screening device for conducting an automated audiometry screening, comprising:
   a tone generator configured to deliver pure tones of different frequencies and intensities;
   an input device;
   a controller device including one or more hardware processors, the controller device arranged to interact with the input device and arranged to iteratively perform the following steps:
      selecting as a test stimulus from the following test stimuli:
         (i) no tone at all,
         (ii) a single tone with a first frequency and a first given intensity, or
         (iii) a plurality of tones of a second frequency and a second given intensity, the second frequency being higher than the first frequency, and each tone of the plurality of tones having a duration that is shorter than a duration of the single tone,
      wherein the controller device is configured to cause each of the test stimuli (i), (ii), and (iii) to be delivered upon selection of the test stimulus;
      applying the selected test stimulus to a test person;
      receiving via the input device from the test person a response indicating which test stimulus was heard by the test person; and
      if the response from the test person indicates that the test stimulus (ii) of the single tone or test stimulus (iii) of the plurality of tones, respectively, was heard by the test person, automatically adjusting the given first or second intensity for a next iteration of a next selected test stimulus, when the next selected test stimulus is test stimulus (ii) of the single tone or test stimulus (iii) of the plurality of tones.

2. The device according to claim 1, further comprising an air-conduction transducer.

3. The device according to claim 1, wherein the input device includes response buttons that are software implemented buttons on a touch screen adaptable to the test person.

4. The device according to claim 1, further comprising
   a microphone configured to measure the ambient noise; and
   an electronic device capable of conducting an ambient noise based trial rejection.

5. The device according to claim 1, wherein the input device includes at least three response buttons.

6. The screening device according to claim 1, wherein the screening device comprises a computer, the controller device being at least a component of the computer.

7. The screening device according to claim 1, wherein the tone generator includes one or more speakers.

8. A screening system for automatedly conducting audiometry screening, comprising:
   a tone generator adapted to deliver tones of different frequencies and intensities;
   an input device;
   a controller device including one or more hardware processors, the controller device arranged to interact with the input device and arranged to iteratively perform the following:
      selecting as a test stimulus from the following test stimuli:
         (i) no tone at all,
         (ii) a single tone with a first frequency and a first given intensity, or
         (iii) a plurality of tones of a second frequency and a second given intensity, the second frequency being higher than the first frequency, and each tone of the plurality of tones having a duration that is shorter than a duration of the single tone,
      wherein the controller device is configured to cause each of the test stimuli (i), (ii), and (iii) to be delivered upon selection of the test stimulus;
      applying the selected test stimulus to a test person;
      receiving via the input device from the test person a response indicating which test stimulus was heard by the test person; and
      if the response from the test person indicates that the test stimulus (ii) of the single tone or test stimulus (iii) of the plurality of tones, respectively, was heard by the test person, automatically adjusting the given first or second intensity for a next iteration of a next selected test stimulus, when the next selected test stimulus is test stimulus (ii) of the single tone or test stimulus (iii) of the plurality of tones.

9. The system according to claim 8, wherein the controller device is arranged to rate the response of the test person if no response is received within a predefined period of time.

10. The system according to claim 8, wherein for each iteration, the test stimulus is randomly selected from the group of available test stimuli (i), (ii), and (iii).

11. The system according to claim 8, comprising a screen that visualizes possible responses to the selected test stimulus for the test person.

12. The system according to claim 8, wherein the controller device is arranged to remove outlier values occurring after a phase of disturbing ambient noise or a short loss of concentration of the test person.

13. The system according to claim 12, comprising a measuring unit configured to measure ambient noise during delivery of the test stimulus, the controller device being configured to reject the response of the test person in case the ambient noise and the test stimulus are of sufficiently similar frequency and the intensity of the ambient noise is of a similar or higher intensity than the test stimulus.

14. The system according to claim 12, wherein a value is characterized as an outlier value if the value is more than a step size away from a previous calculated threshold value in the range between 5 and 10 dB, above or below an overall threshold for a corresponding frequency.

15. The system according to claim 8, wherein the system is arranged to use at most three different frequencies.

16. The system according to claim 8, further comprising an air-conduction transducer.

17. The system according to claim 8, further comprising a headset through which the selected test stimulus is applied to the test person.

\* \* \* \* \*